(12) United States Patent
Gauderer et al.

(10) Patent No.: US 6,361,540 B1
(45) Date of Patent: Mar. 26, 2002

(54) APPARATUS FOR REMOVAL OF ESOPHAGEAL COINS AND SIMILARLY SHAPED OBJECTS

(76) Inventors: Michael W. L. Gauderer, 100 Strathmore Dr., Greer, SC (US) 29650; James M. DeCou, 121 Glen Briar Ct., Simpsonville, SC (US) 29681

( * ) Notice: Subject to any disclaimer, the term of this patent is extended or adjusted under 35 U.S.C. 154(b) by 0 days.

(21) Appl. No.: 09/544,427

(22) Filed: Apr. 6, 2000

(51) Int. Cl.⁷ .................................................. A61C 1/12
(52) U.S. Cl. ...................................... 606/106; 606/206
(58) Field of Search ................................ 606/108, 205, 606/106, 206; 600/114

(56) References Cited

U.S. PATENT DOCUMENTS

| | | | | |
|---|---|---|---|---|
| 686,578 A | * | 11/1901 | Bowersox | 606/106 |
| 3,404,677 A | * | 10/1968 | Springer | 606/206 |
| 3,489,151 A | * | 1/1970 | Eller | 606/106 |
| 3,581,745 A | * | 6/1971 | Eller | 606/106 |
| 5,390,661 A | * | 2/1995 | Griffith et al. | 606/108 |
| 5,474,571 A | * | 12/1995 | Lang | 606/205 |
| 5,620,408 A | * | 4/1997 | Vennes et al. | 600/114 |
| 5,919,206 A | * | 7/1999 | Gengler et al. | 606/205 |
| 6,090,129 A | * | 7/2000 | Ouchi | 606/206 |
| 6,156,055 A | * | 12/2000 | Ravenscroft | 606/206 |

FOREIGN PATENT DOCUMENTS

| | | | | |
|---|---|---|---|---|
| DE | 2800664 | * | 7/1978 | 606/106 |
| DE | 3717658 | * | 12/1988 | 606/106 |

* cited by examiner

Primary Examiner—Cary E. O'Connor
(74) Attorney, Agent, or Firm—Dority & Manning, PA

(57) ABSTRACT

An apparatus developed for the safe, non-surgical removal of coin-like obstructing foreign objects from the esophagus is provided. The technique employs radiologic guidance. The apparatus has a pair of gripping jaws which are inserted through a mouth block and into a patient's esophagus. The apparatus provides a protective sheath surrounding the inserted jaws. A handle, remote from the jaws, is used to extend the jaws from the sheath which then grasp the end-on edge of the obstructing object. The apparatus and obstructing object may then be removed through the bite block as a unit. The technique requires no sedation or general anesthesia and minimizes the risk of collateral injury to the esophageal region.

13 Claims, 6 Drawing Sheets

APPARATUS FOR REMOVAL OF ESOPHAGEAL COINS AND SIMILARLY SHAPED OBJECTS

FIELD OF THE INVENTION

This invention is directed towards an apparatus and process for removing coins or similarly-shaped obstructing objects from the upper esophageal region.

BACKGROUND OF THE INVENTION

Esophageal obstructions by swallowed coins are a frequent occurrence in younger children. Although most ingested coins will pass spontaneously through the intestinal tract, if too large to clear the cricopharyngeal ring, they become impacted in that area. However, there is still much debate as to the best approaches for the removal of such objects. A variety of medical procedures and techniques have been developed for the removal of coins and similarly shaped objects from the upper esophagus.

For instance, endoscopic surgery, employing rigid esophagoscopy, is often selected as a technique for the removal of a coin. Such a procedure has the advantages of offering a clear visualization of the obstructing foreign body and provides a firm engagement and controlled removal of the foreign object. However, endoscopic removal entails the costs of hospital admission and operating room use, costs and risks of general anesthesia, as well as attendant emotional stress on the child's care givers. Likewise, flexible endoscopy or direct laryngoscopy advocated by some practitioners have similar costs and concerns. For coin-like objects which are neither impacted within the esophagus nor irregularly shaped, less invasive and costly procedures are often adopted.

A second approach advocated by some practitioners is the dislodgement of esophageal coins using a Foley balloon catheter. The catheter is inserted through the oral cavity and past the obstruction, followed by the inflation of the balloon. Upon withdrawal of the inflated catheter, the obstructing object is forced upwardly into the oral cavity from where it needs to be expelled or removed. However, the procedure exerts no control over the coin as it passes in proximity to the oropharynx and raises concerns about possible damage to the esophagus, dislodgement into the nasopharynx, or obstruction of the airway.

A third less commonly used alternative is Bougienage displacement, advocated by some, in which a tube-like esophageal dilator is inserted through the esophagus forcing the coin/obstruction downstream and into the stomach. While the coin will thereafter usually pass through the gastrointestinal tract in a subsequent stool, parents are often concerned that the obstructing object is not immediately removed. Further, the bougienage technique is not without some risk of damaging the esophagus.

Accordingly, there remains room for improvement and variation within the art of removal of coins and similar objects which obstruct the upper esophageal region.

SUMMARY OF THE INVENTION

It is an object of the present invention to provide an apparatus and method which affords a rapid and safe removal of a coin from the esophagus of a patient.

It is yet another object of the present invention to provide a removal apparatus which facilitates removal of a coin-like obstructing object from the esophagus of a patient without sedation or anesthesia.

It is still a further object of the present invention to provide a grasping forceps and method which provides a strong, firm grasp of a coin-like obstruction lodged within the esophagus of a patient.

It is still a further object of the present invention to provide a grasping forceps suitable for removing an obstructing object from the esophagus, in which the forceps is surrounded by a flexible hollow sheath which protects the pharyngeal and esophageal tissue guiding the forceps to a proper position within the esophagus directly to the obstructing coin or coin-shaped object.

It is still a further and more particular object of the invention to provide a coin removal tool which is radiopaque.

It is still a further and more particular object of the invention to provide a sterilized kit comprising the necessary and assembled components needed for the fluoroscopic assisted removal of a coin or similar obstructing object from the esophagus of an unsedated patient.

These and other features, aspects, and advantages of the present invention will become better understood with reference to the following description and appended claims.

BRIEF DESCRIPTION OF THE DRAWINGS

A full and enabling disclosure of the present invention, including the best mode thereof, to one of ordinary skill in the art, is set forth more particularly in the remainder of the specification, including reference to the accompanying drawings.

FIGS. 4, 5A and 5B set forth environmental view of the insertion and operation of the removal apparatus;

DESCRIPTION OF THE PREFERRED EMBODIMENT

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents. Other objects, features, and aspects of the present invention are disclosed in, or are obvious from, the following detailed description. It is to be understood by one of ordinary skill in the art that the present discussion is a description of exemplary embodiments only and is not intended as limiting the broader aspects of the present invention, which broader aspects are embodied in the exemplary constructions.

Figures 1A, 1B:
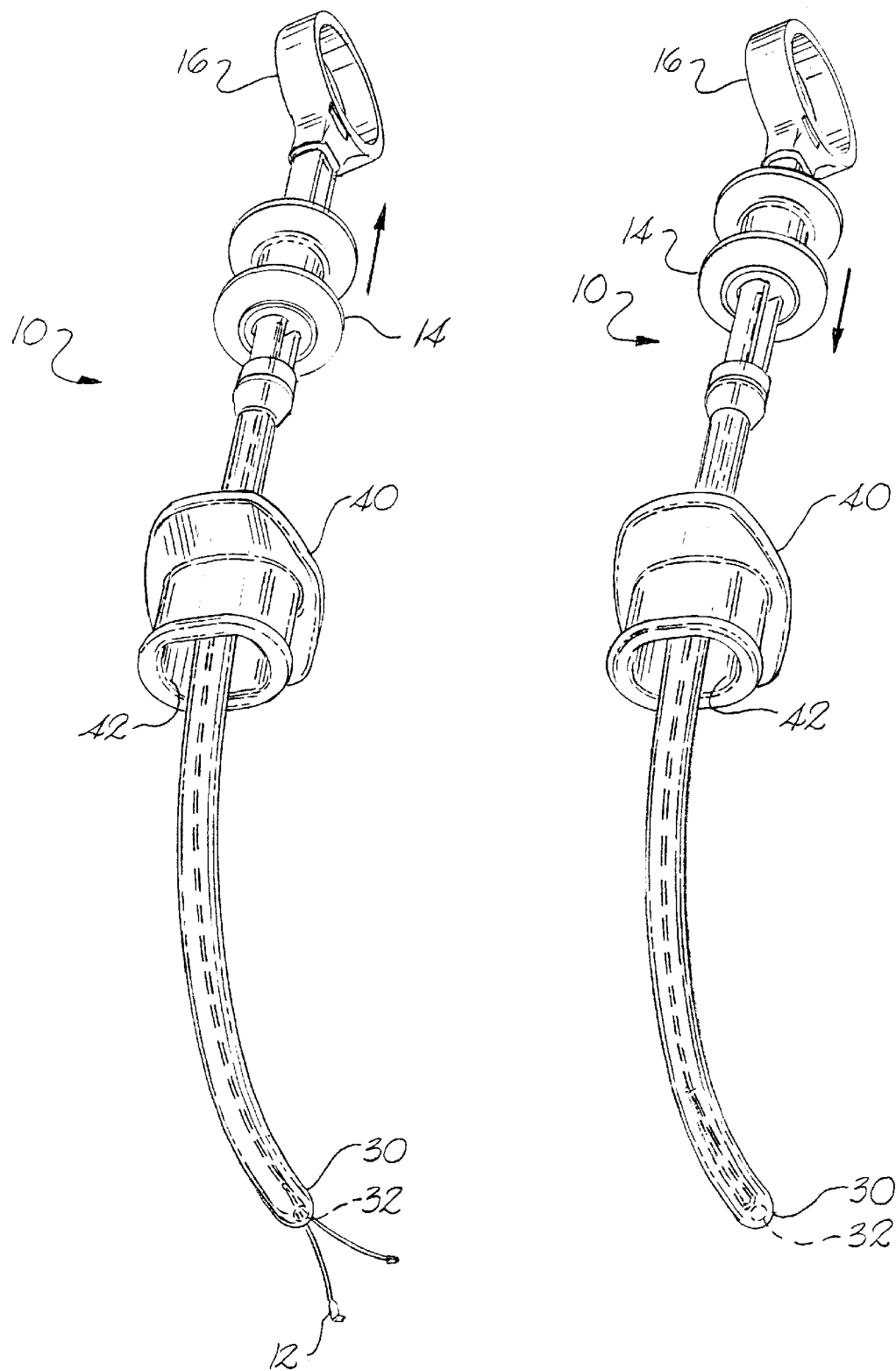
FIGS. 1A and 1B are perspective views of a removal apparatus according to one aspect of the present invention.
Figure 2:
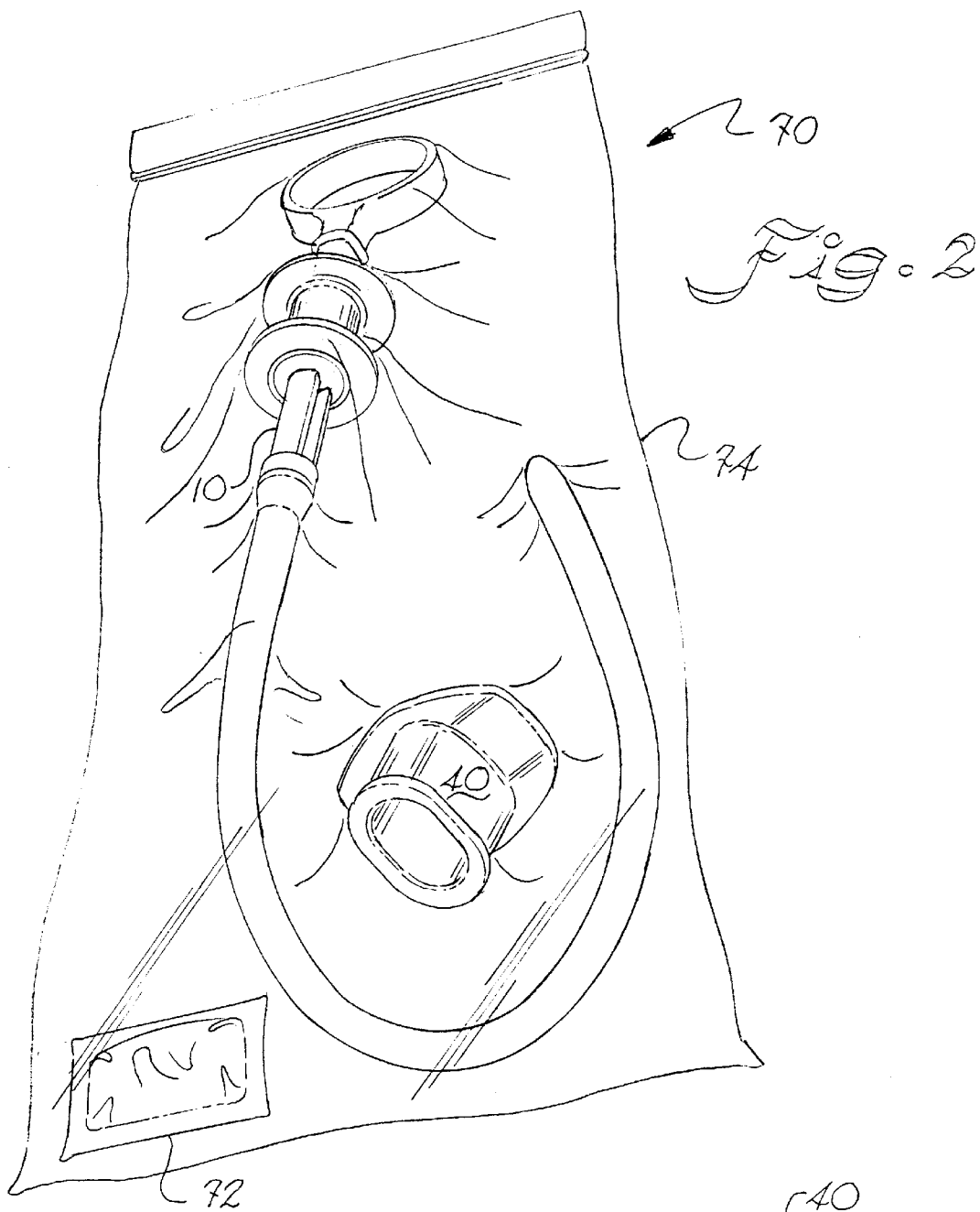
FIG. 2 is a perspective view of a pre-packaged sterilized kit containing the removal tool components of the present invention.

As seen in reference to FIGS. 1A and 1B, a removal tool 10 is set forth having a pair of retractable and reclosable jaws 12 carried by a lower tool end. The construction and operation of jaw 12 is similar to a conventional endoscopic forceps, the construction and use of which is well known in the art. One suitable set of forceps is similar to Olympus Model FG-4L, W-V shape, Olympus Corporation, Lake Success, N.Y. As seen in further reference to FIGS. 1A and 1B, jaws 12 may be opened (FIG. 1B) by moving plunger 14 away from terminal handle 16 as indicated by directional arrows in the figures. As plunger 14 moves, the plunger is connected to a wire or cable 18 which interconnects plunger 14 with jaws 12. Movement of plunger 14 facilitates the reversible opening and closing of jaws 12.

An overall apparatus length of 20 cm has proven useful in terms of a manageable length which affords access to the upper esophageal regions. However, numerous variations in dimensions and shape are possible without compromising the operation of the removal apparatus.

Jaws 12 may be constructed of metal or other radio-opaque material. A radiopaque material helps the visualization of the forceps during fluoroscopy and thereby facilitates positioning and orientation of the jaws with respect to an obstructing object. If desired, the jaws 12 may be provided from a molded plastic or similar rigid material. A radiopaque coating may be used to visualize the jaws or a radio-opaque reference ring or other guide may be incorporated elsewhere upon the removal apparatus.

Figure 6A:
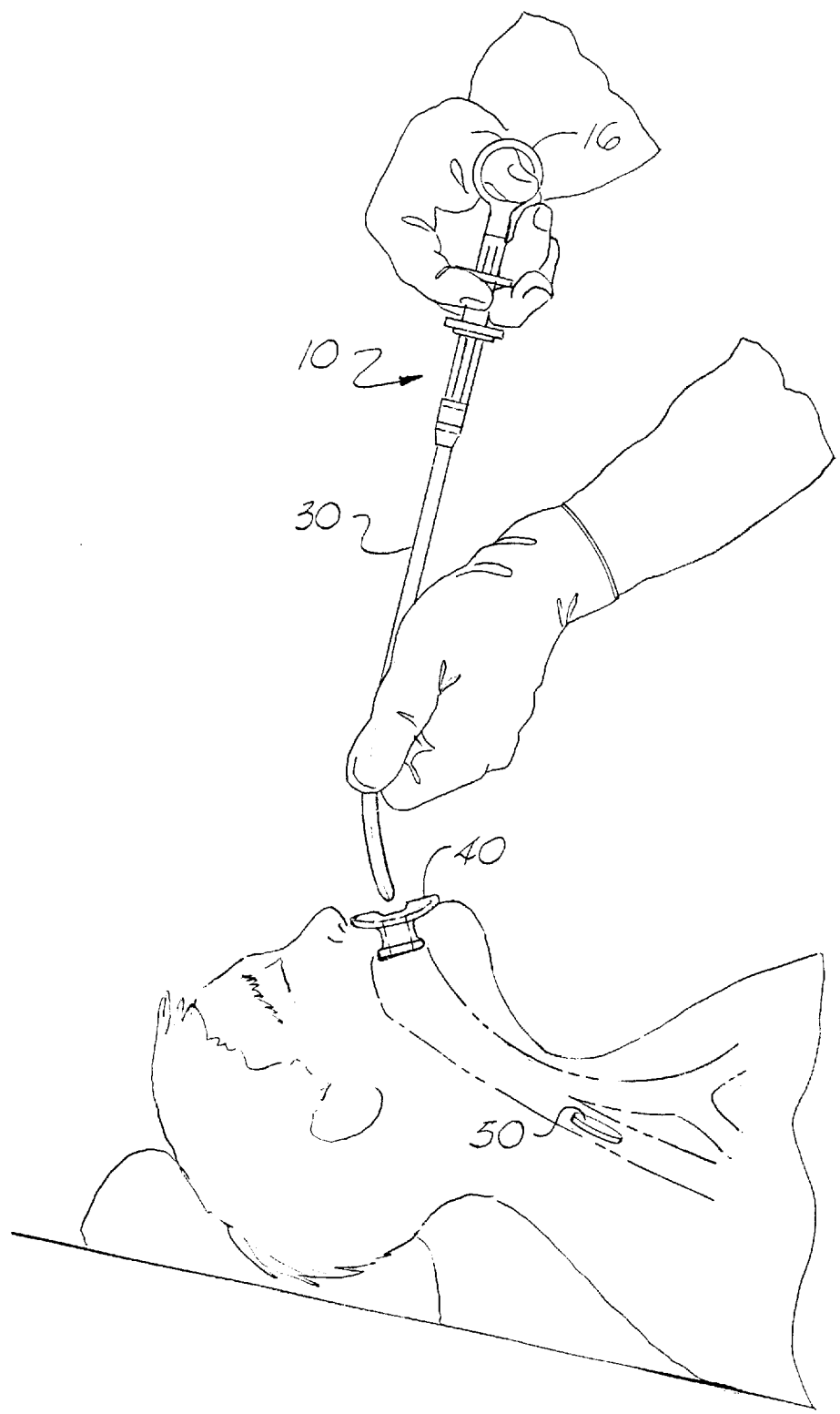
FIGS. 6A–6C are sectional views of the lower tip and in further reference to a coin-like obstruction.
Figure 53:
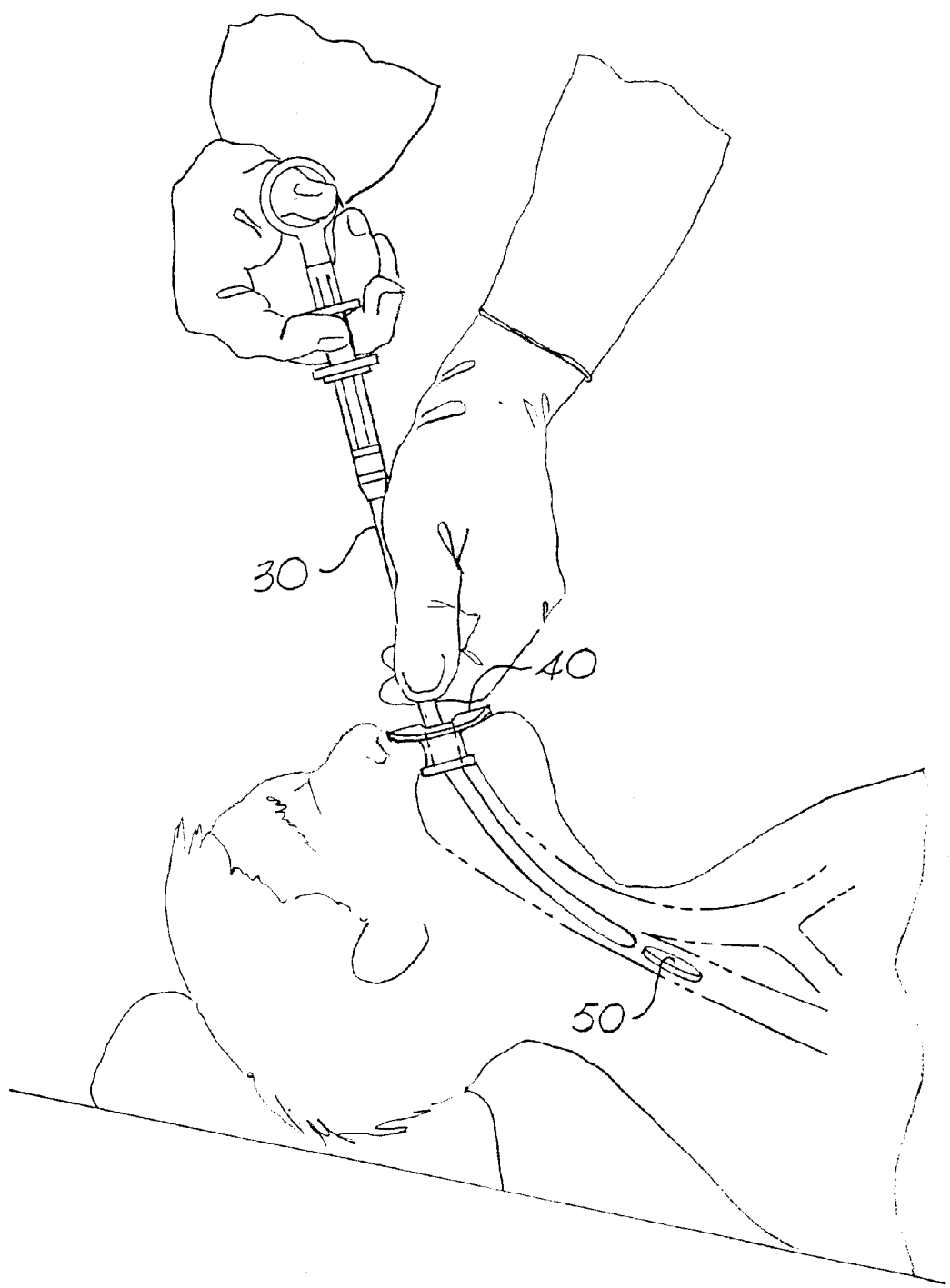
Figure 6A:
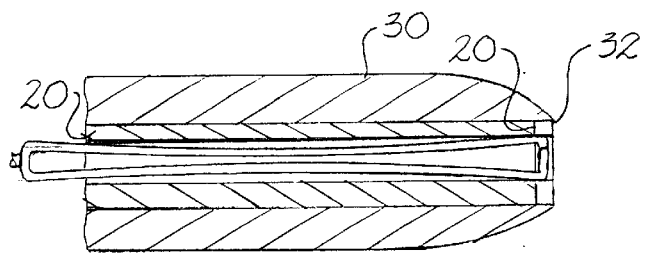
Figure 6B:
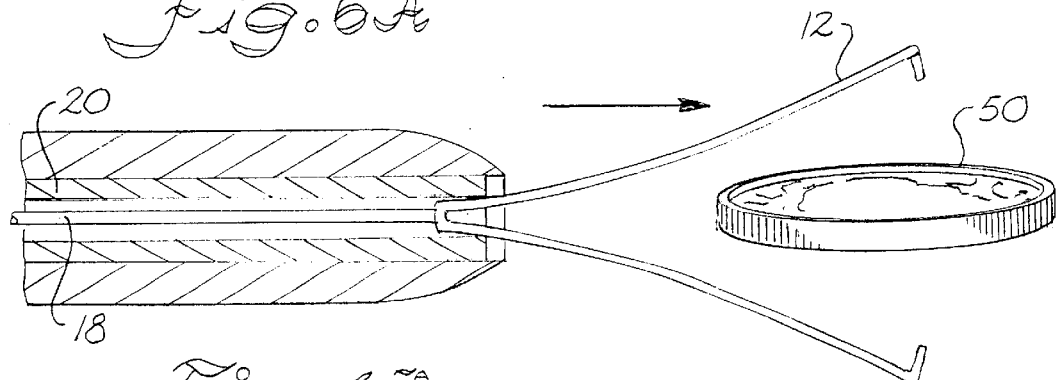
Figure 6C:
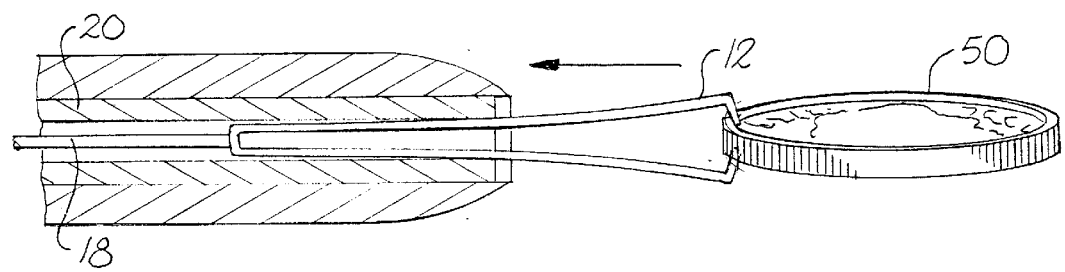
Figure 7:
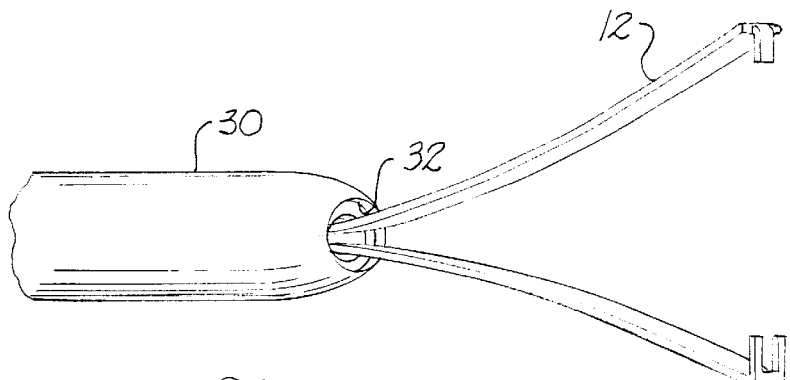
FIG. 7 is a perspective view of the lower tip of the removal apparatus showing details of the sheath and deployed forceps.

A flexible housing 20, as seen in reference to FIGS. 6A–6C in the form of a tubular enclosure, surrounds cable 18. The housing 20 may be provided by a coiled spring-like sheath which surrounds cable 18. A terminal end of housing 20 further defines a receptacle which receives the attached ends of jaws 12 when the jaws are in a retracted position. Jaws 12 have a spring tension which will position the extended forceps in an open, receiving position as seen in FIGS. 6B and 7. As seen in reference to FIGS. 6A and 6C, as the attached jaw ends are retracted into the terminal receptacle of housing 20, the terminal prong ends are thereby closed. Depending upon the design of the jaws and dimensions of housing 20, the terminal jaw ends need not fully retract into the receptacle of housing 20.

The lower end of gripping apparatus 10 further defines a cover seen in the form of a soft, pliable and flexible exterior sheath 30. Sheath 30 may be cylindrical and provided from a silicone rubber similar to materials used in a catheter. The sheath or cover is securely positioned with respect to housing 20. As seen in reference to FIG. 5B, the sheath should extend along the exterior of housing 20 a sufficient distance so that the upper length of the sheath may be grasped by a user when inserted into a patient. A sheath diameter of between 0.40–1.0 cm has been found useful.

One end of sheath 30 defines a hollow tip 32 which extends beyond the lower terminus of housing 20. As best seen in reference to FIG. 6A, when prongs 12 are fully retracted, the terminal tip of prongs 12 are retained within the hollow interior of sheath 30. This arrangement allows for the insertion of the gripping apparatus into the esophagus such that only the soft exterior sheath 30 of the removal apparatus 10 comes into contact with the oropharynx and esophageal walls. If desired, the outer rim of terminal end of sheath 30 may further define a radiopaque ring, coating, or other structure which visualizes the tip region of the removal apparatus 10 during fluoroscopy.

It may be useful to provide a cover 30 having a preestablished memory or curvature. The curvature should approximate the necessary bend required for insertion into the esophageal region of the patient. The existing curvature is believed to limit the amount of contact between the apparatus and the esophageal wall. Further, the curvature helps in the alignment of the removal apparatus with respect to the obstruction in the esophagus.

Figure 3:
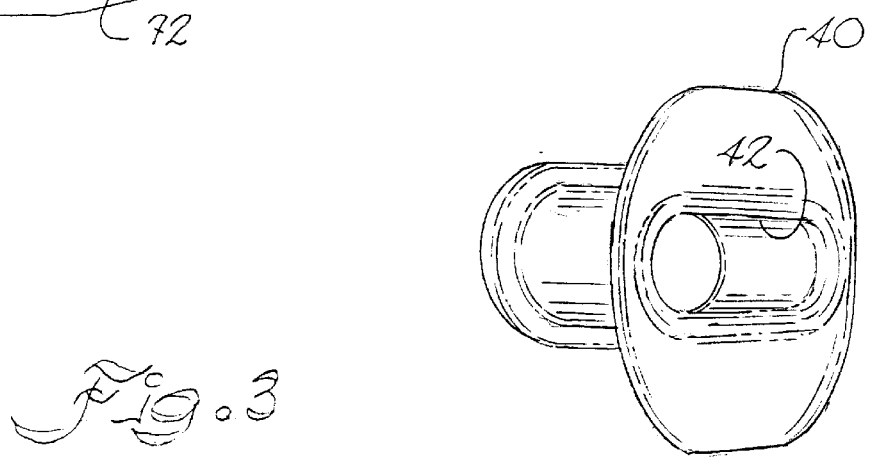
FIG. 3 is a perspective view of a mouth block used in accordance with the present invention.

A block 40 (FIG. 3) is positioned over the sheath 30 via a passage 42 defined along a central axis of block 40. Block 40 is used to engage a patient's mouth and to maintain an open airway as seen in reference to FIGS. 4, 5A, and 5B. It has been found useful to provide a passage 42 having sufficient dimensions that common obstructions such as coins may be withdrawn through the block 40 by the grasping forceps. Accordingly, a preferred block has a passage diameter of at least 2.50 cm which will accommodate the passage of a U.S. quarter or arcade token. This arrangement decreases the overall removal time and avoids having the coin or similar obstruction loose within the patient's throat.

Figure 4:
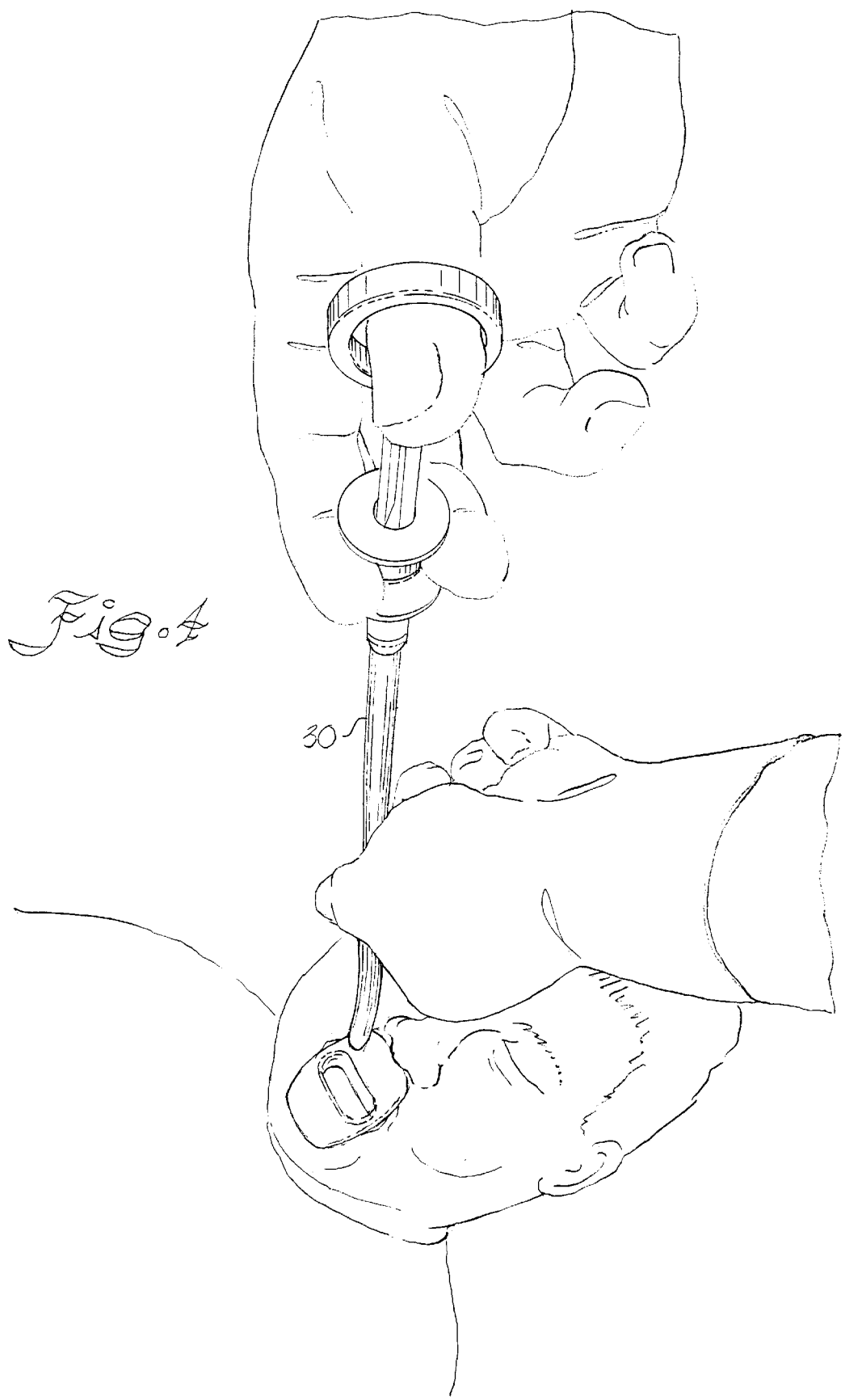

As seen in FIG. 4, block 40 is positioned within the patient's mouth so as to provide a clear passageway for gripping apparatus 10 and to maintain an open airway for the patient. In reference to FIGS. 5A and 5B, gripping apparatus 10 is deployed with its terminal end inserted through passage 42 of block 40. As gripping apparatus is inserted into block 40, the tip 32 is guided into the esophagus of the patient. Progress is monitored via a fluoroscope which visualizes the coin obstruction 50 and the progress of the radiopaque gripping apparatus 10.

Once the gripping apparatus is positioned next to or above the coin, the orientation of jaws 12 may be varied by simple rotation of the gripping apparatus. The jaws are advanced so that the open jaws overlap the periphery of the coin. Upon retraction of the jaws, the coin is firmly grasped and the gripping apparatus and obstructing object are removed as a unit through block 40.

Use of a gripping apparatus has proven effective for the removal of coin-like obstructions lodged within the esophagus of young children. Coin removal is performed under fluoroscopic guidance by appropriately trained personnel with the patient restrained in a supine or lateral decubitus position. The procedure requires neither sedation nor anesthesia and the gripping apparatus is inserted into the esophagus through the block in a method similar to the insertion of a oro-gastric tube. In an evaluation of 28 consecutive patients, ranging in age from 8 months to 8 years, the patients had 29 coins (19 pennies, 2 nickels, 1 dime, 6 quarters and 1 arcade token) removed using the gripping apparatus and process described above. In 22 of the patients, the coin was retrieved following the initial deployment of the forceps' jaws. In 5 patients, a second attempt at grasping the obstruction proved successful. One last patient required four passes for successful removal.

Removal times, as measured from the deployment of the gripping apparatus to removal of the obstruction, took as little as 4 seconds with an average duration of less than 50 seconds. In each instance, no subsequent complications occurred and the patients were discharged to home shortly after removal of the obstructing object.

The gripping apparatus further facilitates the rapid and safe removal of smooth bodied obstructions from a patient's esophagus. No sedation or general anesthesia is needed and the procedure is typically performed in under a minute.

The gripping apparatus facilitates the safe insertion of a pair of gripping forceps without hindering the forceps' deployment and operation. For many situations, the present invention allows removal of an esophageal obstructing foreign body without an operation, involves no sedation or general anesthesia, entails minimal patient discomfort and poses less risk of complications than previously employed treatment options. The tight grasping force of the apparatus allows lodged coins to be extracted and removed. At all times during the removal steps, the coin is maintained under control so as to not pose a further choking hazard while in the patient's mouth. Should the gripping apparatus be unable to remove the obstructing foreign body, the efficacy of established methods of removal have not been compromised. In fact, if the object is small enough to be pushed into the lower esophagus instead of being withdrawn, the effect is the same as the one achieved by the Bougienage technique. The coin-like object should simply now spontaneously travel through the intestinal tract.

One embodiment of the invention includes having the assembled components of the removal apparatus pre-packaged as a sterile kit 70. The components may include a reusable apparatus suitable for repeated use following chemical or steam sterilization. Alternatively, a lower costs disposable unit can be supplied. If a disposable unit employs non-metal or radio transparent materials, a separate radiopaque material may be provided in the form of a ring, coating, or other cover structure to provide an reference point of the apparatus during fluoroscopy.

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention, which is set forth in the following claims. In addition, it should be understood that aspects of the various embodiments may be interchanged, both in whole or in part. Therefore, the spirit and scope of the appended claims should not be limited to the description of the preferred versions contained therein.

That which is claimed is:

1. An apparatus for the removal of foreign objects from the esophagus comprising:
    a pair of forceps having a first end defining a pair of prongs adapted for engaging a flat edge of a foreign object and a handle end for manipulating the terminal pair of prongs between an open engaging position and a closed, retracted position; and,
    a cover which extends over the forceps when the forceps are in the closed position, the cover having a terminal opening for the extension there-through of the pair of prongs when in the open engaging position, the cover further defining a pre-established curvature for facilitating the insertion of the cover and the forceps into the esophageal region of a patient.

2. The apparatus according to claim 1 further comprising a bite block for placement within the mouth of a patient, the bite block defining a passage there-through and engaging therein the cover and the forceps within the passage.

3. The apparatus according to claim 2 wherein the bite block passage defines a diameter of at least 2.5 cm.

4. The apparatus according to claim 1 wherein the pair of forceps comprises a pair of endoscopic forceps.

5. The apparatus according to claim 1 wherein the cover further comprises a radiopaque element.

6. The apparatus according to claim 1 wherein the cover has an outer diameter of between 0.40–1.0 cm.

7. The apparatus according to claim 1 wherein the removal apparatus has a length of about 20 cm.

8. The apparatus according to claim 1 wherein the cover is flexible.

9. A method for removing an esophageal obstruction comprising:
    providing a removal apparatus comprising a pair of forceps housed in a retracted closed position within a cover;
    inserting the removal apparatus through a patient's mouth and into the esophagus adjacent an obstruction;
    extending the forceps from the cover and into an open prong position;
    positioning the prongs along opposing edges of the obstruction;
    grasping the obstruction with the prongs; and,
    withdrawing the removal apparatus and obstruction from the patient.

10. An apparatus for the removal of a foreign object from the esophagus comprising:
    a pair of hinged jaws adapted for engaging a flat edge of a foreign object operatively connected to a handle adapted for manipulating the hinged jaws between an open configuration and a grasping configuration;
    a cover which extends over the hinged jaws when the jaws are in the grasping position, the cover having a terminal opening for the extension there-through of jaws when in the open configuration; and,
    a block for placement within the mouth of a patient, the block defining a passage there-through, the passage adapted for the unrestricted movement of the jaws and cover through the passage.

11. The apparatus according to claim 10 wherein the block passage has a diameter of at least 2.5 cm.

12. The apparatus according to claim 10 wherein the cover further defines a curve for facilitating the insertion of the apparatus into the esophageal region of a patient.

13. The apparatus according to claim 12 wherein the cover further comprises a flexible material.

* * * * *